United States Patent
Zhang et al.

(10) Patent No.: US 7,538,228 B2
(45) Date of Patent: May 26, 2009

(54) OXAZOLINE LIGANDS FOR ASYMMETRIC CATALYSIS

(75) Inventors: Xumu Zhang, State College, PA (US); Duan Liu, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 591 days.

(21) Appl. No.: 11/016,302

(22) Filed: Dec. 17, 2004

(65) Prior Publication Data

US 2005/0137403 A1    Jun. 23, 2005

Related U.S. Application Data

(60) Provisional application No. 60/530,313, filed on Dec. 17, 2003.

(51) Int. Cl.
*C07F 9/50*      (2006.01)
*C07D 277/10*   (2006.01)
*C07D 263/10*   (2006.01)
*C07D 233/20*   (2006.01)
*C07D 207/20*   (2006.01)

(52) U.S. Cl. .............. 548/119; 548/413; 548/146; 548/237; 548/354.1; 548/577

(58) Field of Classification Search .......... 548/119, 548/146, 237, 354.1, 413, 577
See application file for complete search history.

(56) References Cited

U.S. PATENT DOCUMENTS 3,268,544 A * 8/1966 Thompson et al. .......... 548/146

6,472,533 B1   10/2002  Burgess ....................... 548/119

OTHER PUBLICATIONS

PCT International Search Report and Written Opinion dated Aug. 18, 2005 from PCT International Application No. PCT/US04/42850.

* cited by examiner

*Primary Examiner*—Rei-Tsang Shiao
*Assistant Examiner*—Joseph R Kosack
(74) *Attorney, Agent, or Firm*—Ohlandt, Greeley, Ruggiero & Perle, L.L.P.

(57) ABSTRACT

A chiral ligand represented by the formula and its enantiomer:

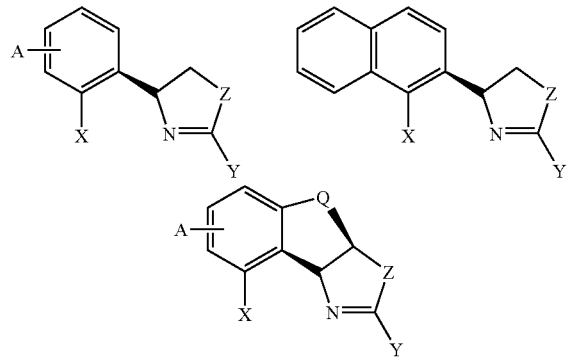

wherein A, X, Y and Z are as defined in the specification is provided. Also provided is a process of making the chiral ligands and catalysts prepared from these ligands and a transition metal, a salt thereof or a complex thereof. In addition, a method of preparing an asymmetric compound by a transition metal catalyzed asymmetric reaction, such as, hydrogenation, hydride transfer reaction, hydrosilylation, hydroboration, hydrovinylation, hydroformylation, hydrocarboxylation, allylic alkylation, epoxidation, cyclopropanation, Diels-Alder reaction, Aldol reaction, ene reaction, Heck reaction and Michael addition is provided.

12 Claims, No Drawings

OXAZOLINE LIGANDS FOR ASYMMETRIC CATALYSIS

This application claims priority from U.S. Provisional Application Ser. No. 60/530,313, filed Dec. 17, 2003.

FEDERALLY SPONSORED RESEARCH OR DEVELOPMENT

This invention was made with government support under Grant No. 1R01 GM58832, awarded by the National Institutes of Health. The Government has certain rights in the invention.

BACKGROUND OF THE INVENTION

1. Field of the Invention

The present invention relates to novel oxozalines and their derivatives as ligands and their applications in asymmetric catalysis. More particularly, the present invention relates to transition metal complexes of these ligands such as oxozalines, bis-oxozalines, phosphine oxozalines.

2. Description of the Prior Art

Development of new chiral ligands is important for transition metal-catalyzed asymmetric reactions. Among the most commonly used transition metal catalysts for asymmetric hydrogenation, Ir-based systems remain far from maturity compared to Rh or Ru-based systems (Ohkuma, T.; Kitamura, M.; Noyori R. *Catalytic Asymmetric Synthesis* (Ed.: Ojima, I.), 2nd ed., Wiley, New York, 2000).

Oxazoline ligands have been introduced by Pfaltz, and others as effective ligands for transition-metal catalyzed asymmetric hydrogenation and C—C bond forming reactions (*Comprehensive Asymmetric Catalysis, Vol.* 1+3 (Eds. Jacobsen, E. N.; Pfaltz, A.; Yamamoto H.), Springer, Berlin, 1999). One well-known Ir-complex was the Crabtree catalyst (R. Crabtree, *Acc. Chem. Res.*, 1979, 12, 331-338), which was highly efficient for hydrogenation of unfunctionalized polysubstituted olefins, a type of substrates remaining difficult to be reduced with Rh or Ru catalysts.

A series of P, N ligands have been introduced by Pfaltz, Burgess and others for asymmetric hydrogenation of alkenes, ketones and imines (A. Pfaltz, J. Blankenstein, R. Hilgraf, E. Hormann, S. McIntyre, F. Menges, M. Schonleber, S. P. Smidt, B. Wustenberg, N. Zimmermann, *Adv. Synth. Catal.*, 2003, 345, 33-43 and references therein; b) T. Bunlaksananusorn, K. Polborn, P. Knochel, *Angew. Chem. Int. Ed.* 2003, 42, 3941-3943; c) G. Xu, S. R. Gilbertson, *Tetrahedron Lett.* 2003, 44, 953-955; d) D. J. Brauer, K. W. Kottsieper, S. Boβenbach, O. Stelzer, *Eur. J. Inorg. Chem.* 2003, 1748-1755; e) W. Tang, W. Wang, X. Zhang, *Angew. Chem. Int. Ed.* 2003, 42, 943-946; f) F. Menges., M. Neuburger, A. Pfaltz, *Org. Lett.* 2002, 4, 4713-4716; g) D. Hou, J. Reibenspies, T. J. Colacot, K. Burgess, *Chem. Eur. J.* 2001, 7, 5391-5400).

Most of these catalysts suffer from problems, such as highly substrate dependent and relativity low turnovers. Thus, the development of new efficient chiral ligands for Ir-catalyzed hydrogenation is still needed and challenging.

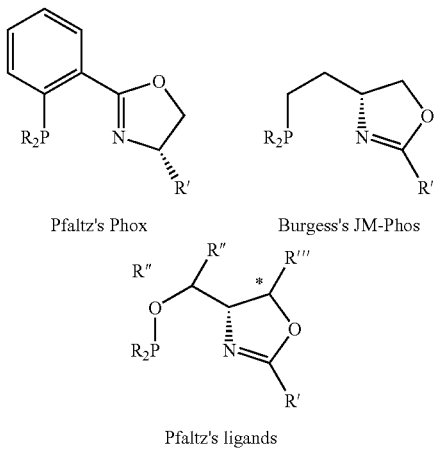

Pfaltz's Phox     Burgess's JM-Phos

Pfaltz's ligands

The conformational rigidity of a chiral ligand has been demonstrated to be an important factor for high enantioselectivity in asymmetric catalysis. Bidentate ligand with a more rigid linker between the two coordinating sites can form a more rigid metal cycle with reduced possibilities of different conformers, and thus, enhance the enantioface differentiation.

JM-Phos, reported by Burgess, exhibited very good enantioselectivities in Ir-catalyzed hydrogenation of several olefins (Preparation of oxazoline substituted phosphine ligands for chiral catalysis (Burgess, Kevin, U.S. Pat. No. 6,472,533 B1). However, the ethylene linker between the phosphine part and oxazoline part is too flexible to deliver the maximum of asymmetric induction from the chiral ligand.

We envision that new ligands might be superior to JM-Phos due to their more rigid 1,2-phenyl linker, in which R and R' are either alkyl, substituted alkyl, aryl or substituted aryl groups.

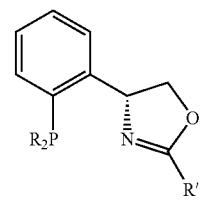

Conformationally rigid new P,N ligands for asymmetric catalysis

The inexpensive enantiomerically pure phenyl glycinol are widely used as a building block in chiral ligand synthesis. However, ortho-substituted phenyl glycinol are rarely used due to the lacking of efficient synthesis procedure (P. O'Brien, S. A. Osborne, D. D. Parker, *J. Chem. Soc., Perkin Trans.* 1, 1998, 2519-2526).

One of most direct ways to make ligands would be based on ortho-substitution of phenyl glycinol. Thus, developing an efficient method of ortho-substitution of phenyl glycinol was needed. Although α-N,N-dimethylamino group was commonly used as an ortho-directing group for metallation of aromatic rings (T. Ireland, G. Grossheimann, C. Wieser-Jeunesse, P. Knochel, *Angew. Chem. Int. Ed.* 1999, 38, 3212-3215), directly using primary amines for such a purpose was less explored and was not used to construct chiral ligands (S.

A. Burns, R. J. P. Corriu, V. Huynh, J. J. E. Moreau, *J. Organomet. Chem.* 1987, 333, 281-290).

We have successfully carried out, for the first time, an ortho-lithiation of silyl-protected phenyl glycinol. Subsequent reaction with $I_2$ or different phosphine chlorides efficiently gave rise to 2-iodo or 2-phosphino phenyl glycinol derivatives, which are novel and highly modular chiral synthons for ligand synthesis.

On the basis of this method, practical routes have been developed for making a number of new chiral ligands. Exploration of these ligand motifs has lead to construction of arrays of chiral ligands that can be used to prepare transition metal-catalysts which, in turn, can be used in a variety of transition metal-catalyzed asymmetric reactions, including, for example, hydrogenation, hydride transfer reaction, hydrosilylation, hydroboration, hydrovinylation, hydroformylation, hydrocarboxylation, allylic alkylation, epoxidation, cyclopropanation, Diels-Alder reaction, Aldol reaction, ene reaction, Heck reaction or Michael addition.

SUMMARY OF THE INVENTION

The present invention provides a chiral ligand selected from compounds represented by the following formulas and their enantiomers:

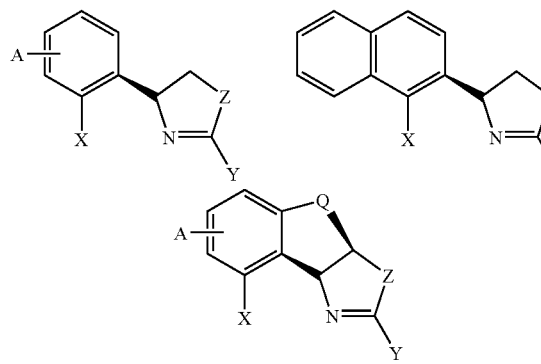

where X is selected from:

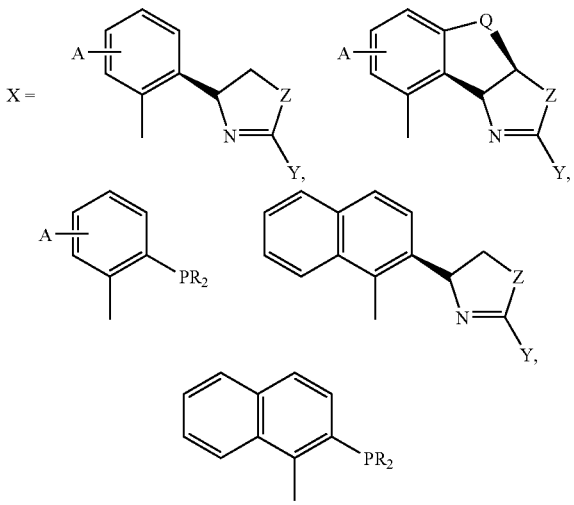

$PR_2$, $P(OR)_2$, $P(NR_2)_2$, $PCl_2$, phosphocycle, P-chiral phospholane, Cl, Br, I, OH, SR, $NH_2$, COOR, COOH, and R;

wherein each R is independently selected from: linear, branched or cyclic alkyl, linear, branched or cyclic substituted alkyl, aryl, substituted aryl, and a hetereocyclic group;

wherein Y is selected from: linear, branched or cyclic alkyl, linear, branched or cyclic substituted alkyl, aryl, substituted aryl, ferrocene, substituted ferrocene, a heterocyclic group, and a hetereoaromatic group;

A is a substituent on the aromatic ring selected from: hydrogen, halide, alkoxyl, carboxylates, linear, branched or cyclic alkyl, aryl, and a substituted aryl group;

Z is selected from: oxygen, sulfur, NH, NR, and $CH_2$; and

Q is selected from: $CH_2$ and $CH_2CH_2$.

The present invention further provides a catalyst formed from the above ligands and a transition metal, a salt thereof, or a complex thereof. The catalyst is prepared by a process including the step of: contacting a transition metal, a salt thereof, or a complex thereof, and a chiral ligand selected from compounds represented by the following formulas and their enantiomers:

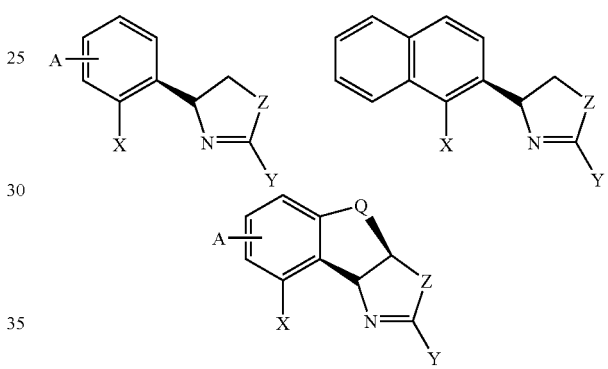

where X is selected from:

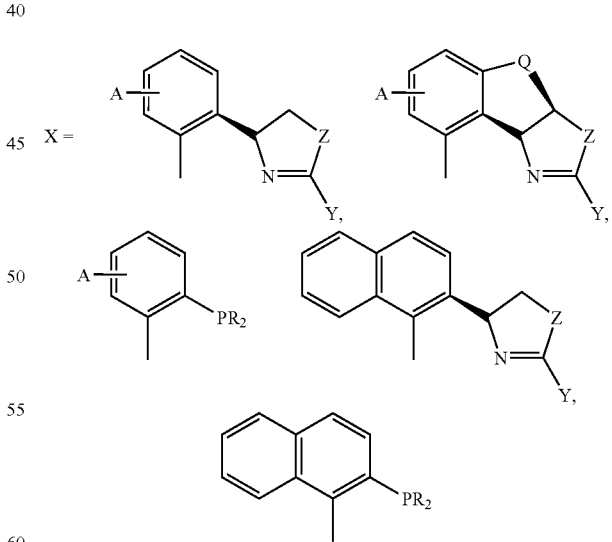

$PR_2$, $P(OR)_2$, $P(NR_2)_2$, $PCl_2$, phosphocycle, P-chiral phospholane$_2$, Cl, Br, I, OH, SR, $NH_2$, COOR, COOH, and R;

wherein each R is independently selected from: linear, branched or cyclic alkyl, linear, branched or cyclic substituted alkyl, aryl, substituted aryl, and a hetereocyclic group;

wherein Y is selected from: linear, branched or cyclic alkyl, linear, branched or cyclic substituted alkyl, aryl, substituted aryl, ferrocene, substituted ferrocene, a heterocyclic group, and a hetereoaromatic group;

A is a substituent on the aromatic ring selected from: hydrogen, halide, alkoxyl, carboxylates, linear, branched or cyclic alkyl, aryl, and a substituted aryl group;

Z is selected from: oxygen, sulfur, NH, NR, and CH$_2$; and

Q is selected from: CH$_2$ and CH$_2$CH$_2$.

The present invention also provides a method of preparing an asymmetric compound by a transition metal catalyzed asymmetric reaction. The method includes the step of:

contacting a substrate and a reactant for an asymmetric reaction in the presence of a catalyst at a temperature, pressure and for a length of time sufficient to produce the asymmetric compound;

wherein the asymmetric reaction is selected from: hydrogenation, hydride transfer reaction, hydrosilylation, hydroboration, hydrovinylation, hydroformylation, hydrocarboxylation, allylic alkylation, epoxidation, cyclopropanation, Diels-Alder reaction, Aldol reaction, ene reaction, Heck reaction and Michael addition; and wherein the catalyst prepared by a process including: contacting a transition metal, a salt thereof, or a complex thereof, and a chiral ligand selected from compounds represented by the following formulas and their enantiomers:

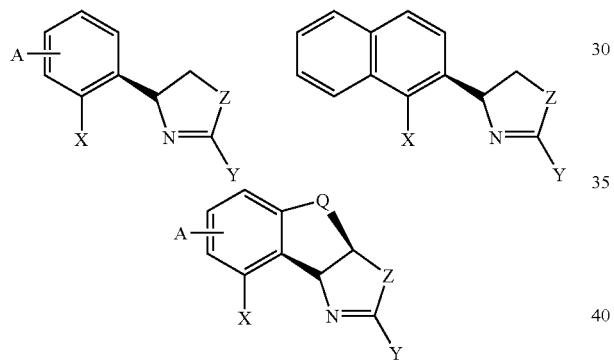

where X is selected from:

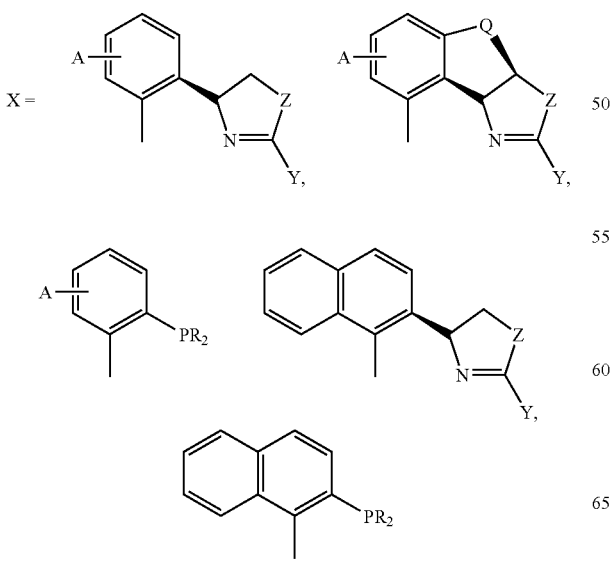

PR$_2$, P(OR)$_2$, P(NR$_2$)$_2$, PCl$_2$, phosphocycle, P-chiral phospholane$_2$, Cl, Br, I, OH, SR, NH$_2$, COOR, COOH, and R; wherein each R is independently selected from: linear, branched or cyclic alkyl, linear, branched or cyclic substituted alkyl, aryl, substituted aryl, and a heterocyclic group; wherein Y is selected from: linear, branched or cyclic alkyl, linear, branched or cyclic substituted alkyl, aryl, substituted aryl, ferrocene, substituted ferrocene, a heterocyclic group, and a hetereoaromatic group; wherein A is a substituent on the aromatic ring selected from: hydrogen, halide, alkoxyl, carboxylates, linear, branched or cyclic alkyl, aryl, and a substituted aryl group; wherein Z is selected from: oxygen, sulfur, NH, NR, and CH$_2$; and wherein Q is selected from: CH$_2$ and CH$_2$CH$_2$.

The present invention still further provides a process for preparing the ligands according to the present invention including an ortho-substitution step. The process includes the step of contacting:

(i) a chiral compound selected from compounds represented by the following formulas and their enantiomers:

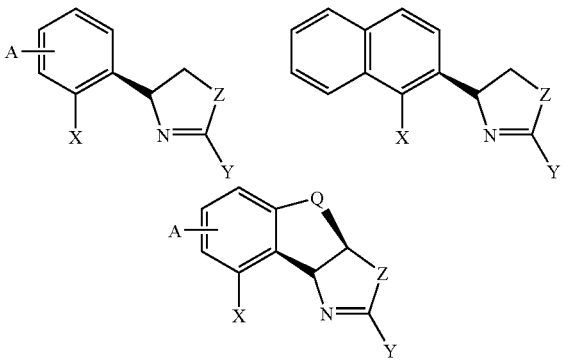

where X is a leaving group; and (ii) an a compound of the formula M-W, wherein M is a metal selected from: Li, Na, Cu, and MgX; and wherein W is anion selected from:

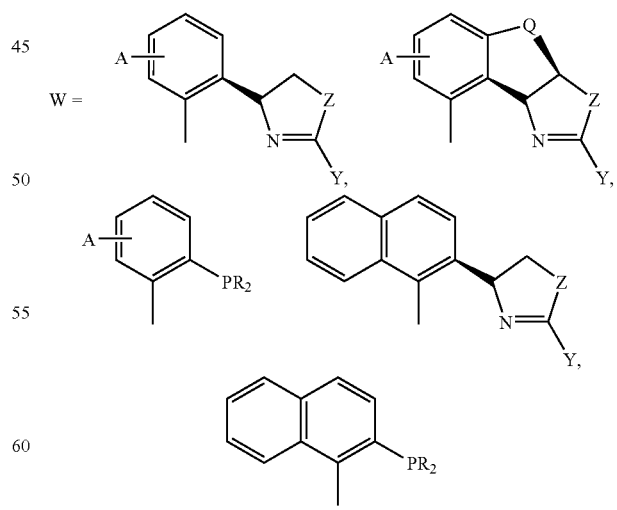

—PR$_2$, —P(OR)$_2$, —P(NR$_2$)$_2$, phosphocycle, P-chiral phospholane$_2$, —SR, NR$_2$, and R; wherein each R is independently selected from: linear, branched or cyclic alkyl, linear, branched or cyclic substituted alkyl, aryl, substituted aryl, and a hetereocyclic group; wherein Y is selected from: linear, branched or cyclic alkyl, linear, branched or cyclic substituted alkyl, aryl, substituted aryl, ferrocene, substituted ferrocene, a hetereocyclic group, and a hetereoaromatic group; wherein A is a substituent on the aromatic ring selected from: hydrogen, halide, alkoxyl, carboxylates, linear, branched or cyclic alkyl, aryl, and a substituted aryl group; wherein Z is selected from: oxygen, sulfur, NH, NR, and $CH_2$; and wherein Q is selected from: $CH_2$ and $CH_2CH_2$;

wherein the contacting is carried out at a temperature, pressure and for a length of time sufficient to produce the chiral ligand.

DETAILED DESCRIPTION OF THE INVENTION

Despite that a number of chiral oxozalines, bis-oxozolines, phosphine oxozolines ligands be prepared, the chiral cavity is generally not deep for dictating highly enantioselective transformations, some chiral ligands are difficult to be prepared, and a number of chiral ligands are conformationally flexible.

In the present invention, we introduce an oxozoline prepared from chiral aryl amino alcohols and an acid.

Derivatives of these oxozolines can be used to prepared a number of new oxazolines, bis-oxazolines and phosphine oxazolines. The resulting compounds are useful for asymmetric catalytic reactions.

Since some aryl amino alcohols are readily available, the corresponding chiral ligands can be prepared for practical asymmetric reactions.

Introducing the aryl group from the aryl amino alcohols increase the conformational rigidity, which is critical for some asymmetric transformations.

Scheme A

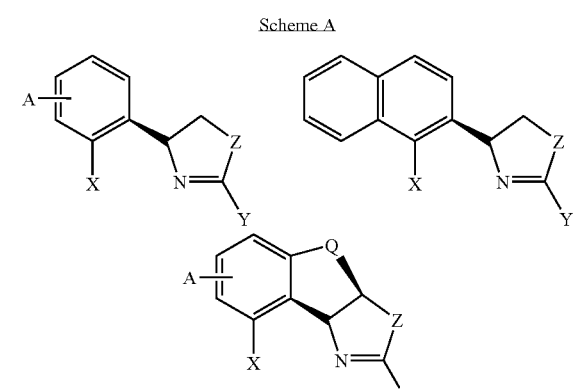

X = $PR_2$, $P(OR)_2$, $P(NR_2)_2$, $PCl_2$, P-chiral phospholane$_2$

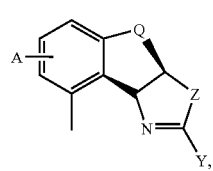

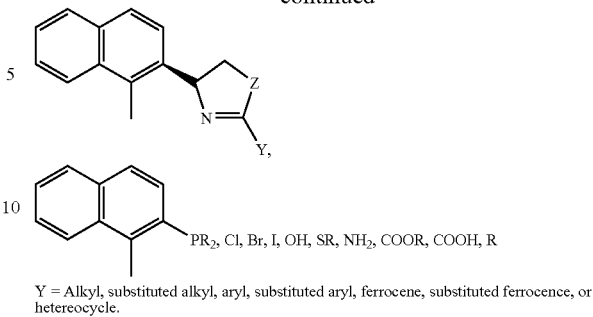

Y = Alkyl, substituted alkyl, aryl, substituted aryl, ferrocene, substituted ferrocence, or hetereocycle.

In these ligands, R is an alkyl, aryl, substituted alkyl, substituted aryl, heterocyclic group; $X=PR_2$, $P(OR)_2$, $P(NR_2)_2$, $PCl_2$, phosphocycle, Cl, Br, OH, SR, $NH_2$, COOR, COOH, R, groups described in the scheme A; Y is an alkyl, substituted alkyl, aryl, substituted aryl, ferrocene, substituted ferrocene, heterocycles, heteroaromatics; A represent substitution on the aromatic ring, including hydrogen, halide, alkoxy, carboxylates, alkyl, aryl, cyclic substitution; Z is an oxygen, sulfur, NH, NR, $CH_2$; Q is a $CH_2$ or $CH_2CH_2$.

Thus, the present invention provides a chiral ligand which can be a compound represented by the formula or its enantiomer:

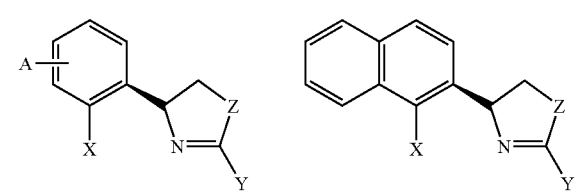

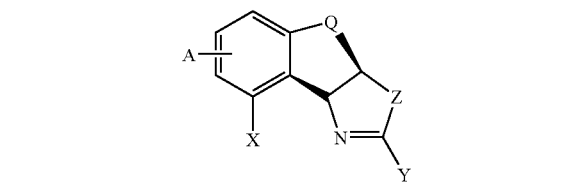

wherein X is a groups represented by the following formulas:

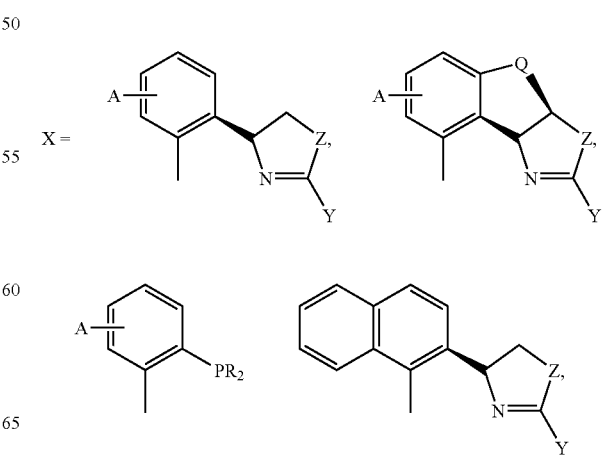

-continued

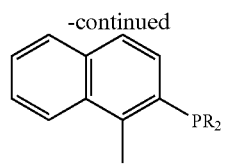

PR$_2$, P(OR)$_2$, P(NR$_2$)$_2$, PCl$_2$, phosphocycle, P-chiral phospholane, (P-chiral phospholane)$_2$, Cl, Br, OH, SR, NH$_2$, COOR, COOH, R, and groups described in scheme A;

R is an alkyl, aryl, substituted alkyl, substituted aryl, hetereocyclic group; Y is an alkyl, substituted alkyl, aryl, substituted aryl, ferrocene, substituted ferrocene, hetereocycles, or heteroaromatics;

A is a substituent on the aromatic ring, which can be hydrogen, halide, alkoxyl, carboxylates, alkyl, aryl, or a cyclic group;

Z is oxygen, sulfur, NH, NR, or CH$_2$; and

Q is CH$_2$ or CH$_2$CH$_2$.

The term "phosphocycle" in the context of the present invention means any cyclic system containing phosphorus atom(s) in a ring. The term "P-chiral phospholane" is an example of a 5-membered ring phosphocycle and "(P-chiral phospholane)$_2$" is a dimeric example thereof.

In a preferred embodiment, the chiral ligand according to the present invention is represented by the above formulas, wherein:

each R is independently selected from: an alkyl, aryl, substituted alkyl, substituted aryl, and hetereocyclic group;

Y is selected from: linear, branched or cyclic alkyl, linear, branched or cyclic substituted alkyl, aryl, and substituted aryl;

A is selected from: hydrogen, halide, alkoxyl, carboxylates, linear, branched or cyclic alkyl, aryl, and a substituted aryl group;

Z is selected from: oxygen, sulfur, NH, NR, and CH$_2$; and

Q is selected from: CH$_2$ and CH$_2$CH$_2$.

Preferably, each R and Y is independently selected from an alkyl of 1-12 carbon atoms. More preferably, each R and Y is independently selected from: methyl, ethyl, propyl, butyl, pentyl, cyclopentyl, hexyl, cyclohexyl, octyl, isomers thereof. Most preferably, each R and Y is independently selected from an aryl group of 6-15 carbon atoms.

In a particularly preferred embodiment, each R and Y is independently selected from: phenyl, tolyl, mesityl, xylyl, biphenylyl and naphthyl.

In one aspect, the chiral ligand is represented by the following formulas and their enantiomers:

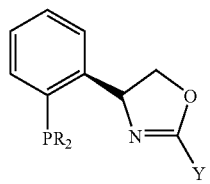 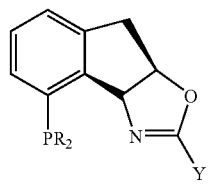

wherein each R is independently selected from: an alkyl, aryl, substituted alkyl, substituted aryl, and hetereocyclic group; and Y is independently selected from: linear, branched or cyclic alkyl, linear, branched or cyclic substituted alkyl, aryl, and substituted aryl.

Preferably, each R and Y is independently selected from an alkyl of 1-12 carbon atoms. More preferably, each R and Y is independently selected from: methyl, ethyl, propyl, butyl, pentyl, cyclopentyl, hexyl, cyclohexyl, octyl, and isomers thereof. Most preferably, each R and Y is independently selected from an aryl group of 6-15 carbon atoms.

In a particularly preferred embodiment, each R and Y is independently selected from: phenyl, tolyl, mesityl, xylyl, biphenylyl and naphthyl.

In another aspect, the chiral ligand is represented by the following formulas and their enantiomers:

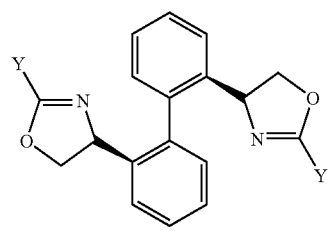

wherein each Y is independently selected from: linear, branched or cyclic alkyl, linear, branched or cyclic substituted alkyl, aryl, substituted aryl, ferrocene, substituted ferrocene, a hetereocyclic group, and a hetereoaromatic group.

Preferably, each Y is independently selected from: linear, branched or cyclic alkyl of 1-12 carbon atoms. More preferably, each Y is independently selected from: methyl, ethyl, propyl, butyl, pentyl, cyclopentyl, hexyl, cyclohexyl, octyl, and isomers thereof. Most preferably, each Y is independently selected from an aryl group of 6-15 carbon atoms.

In a particularly preferred embodiment, each Y is independently selected from: phenyl, tolyl, mesityl, xylyl, biphenylyl and naphthyl.

To illustrate the structure of new ligands, Schemes 1-4 indicate some of ligands that can be prepared. These ligands have a general structure described in the summary of invention.

Scheme 1

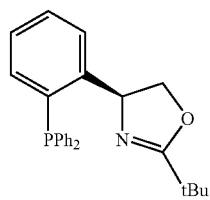

L1

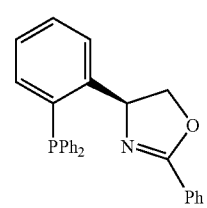

L2

-continued
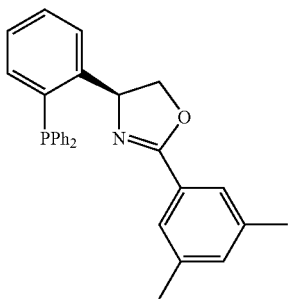
L3
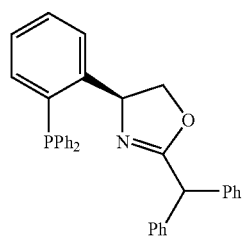
L4
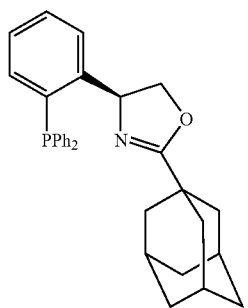
L5
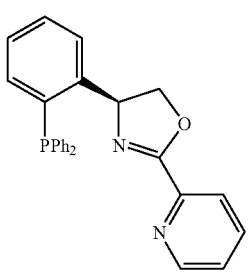
L6
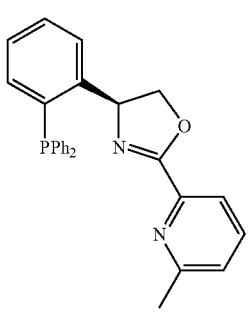
L7
-continued
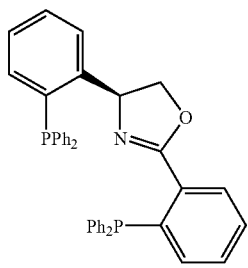
L8
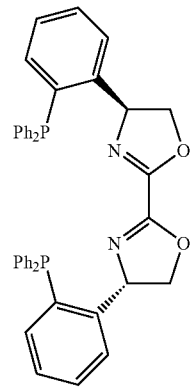
L9
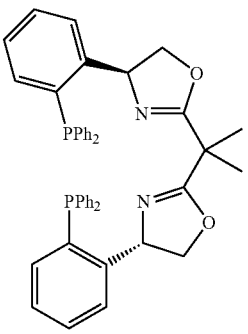
L10
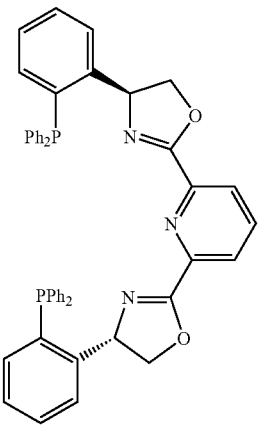
L11
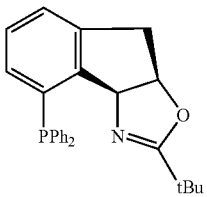
L12

-continued

L13

L14

L15

L16

L15

L16

L17

-continued

L18

Scheme 2

L19

L20

L21

L22

L23

-continued
L24
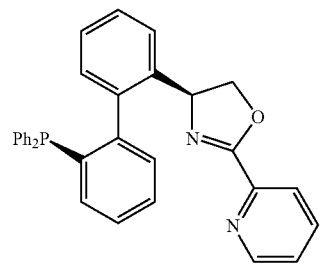
L25
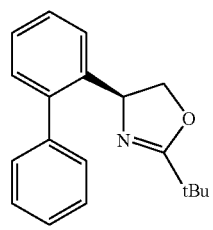
L26
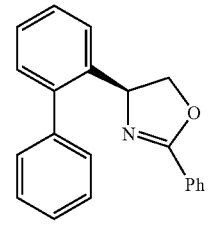
L27
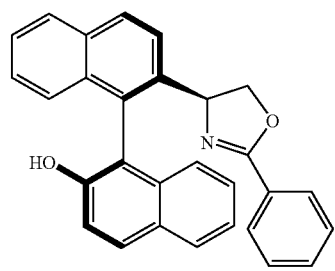
L28
L29
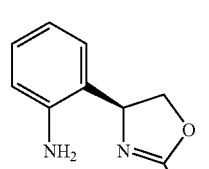
L30
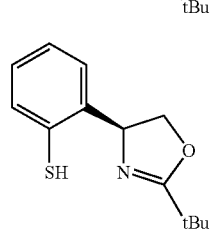
-continued
L31
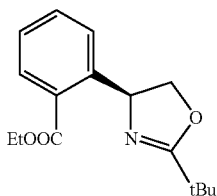
L32
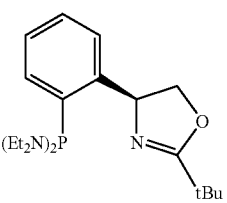
L33
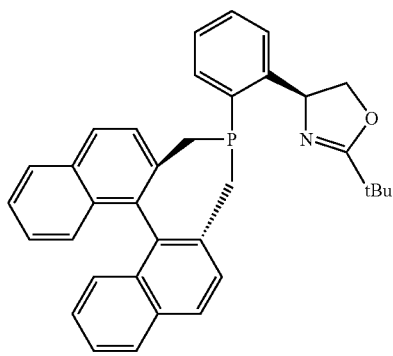
L34
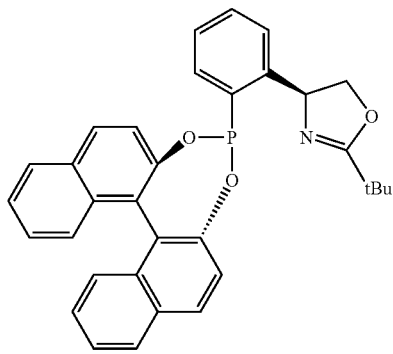
Scheme 3
L35
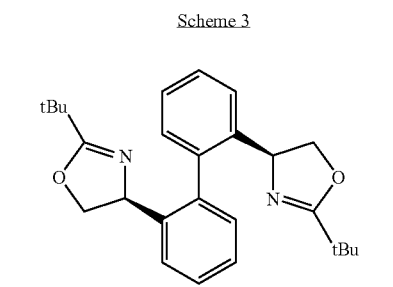

-continued
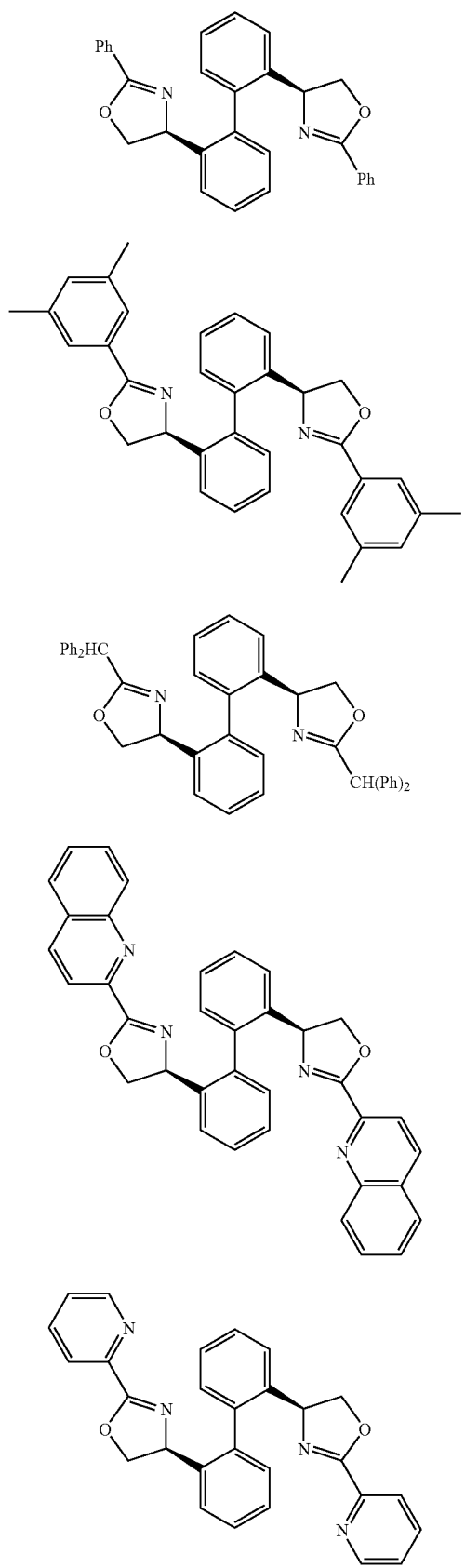
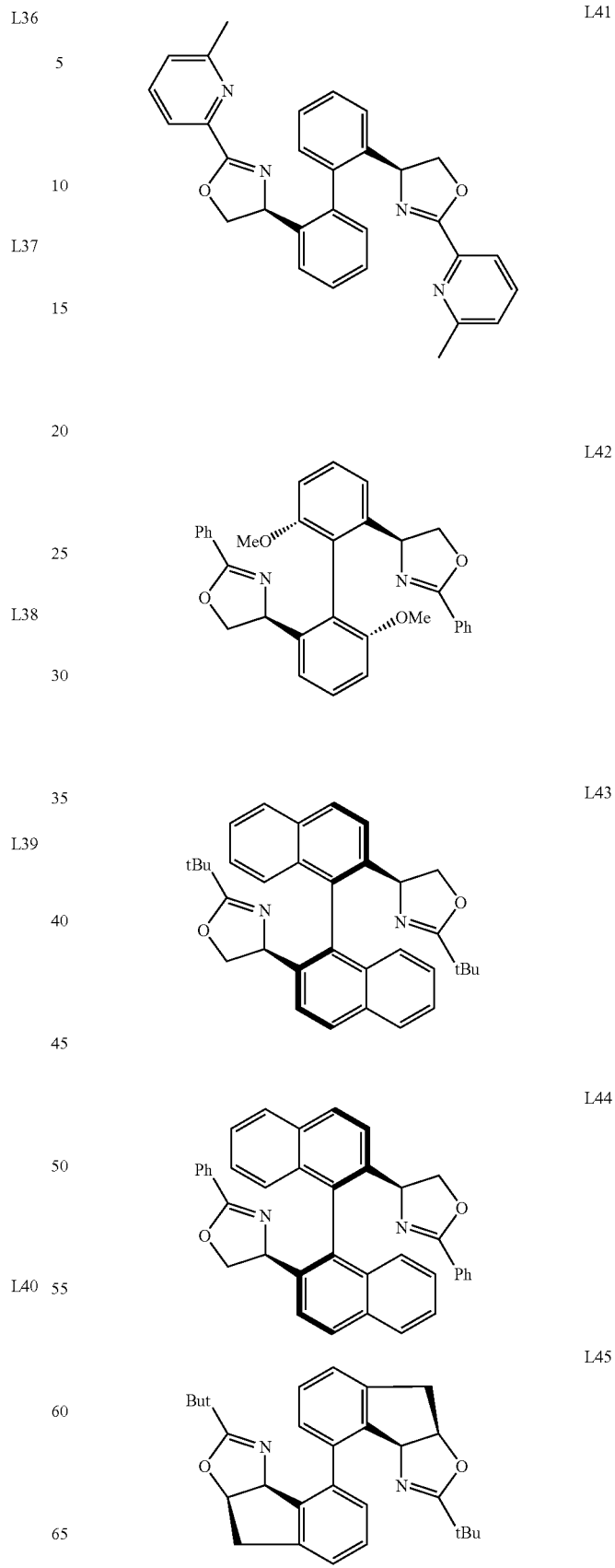

-continued
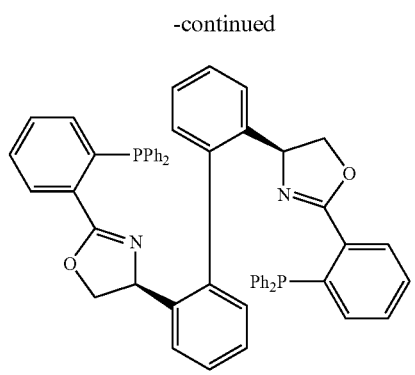
L46
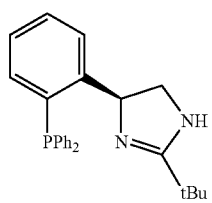
L47
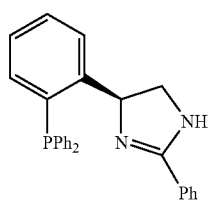
L48
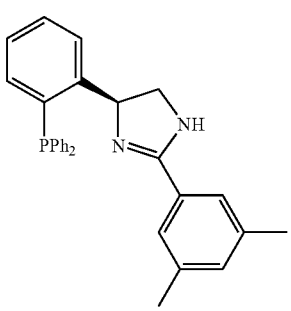
L49
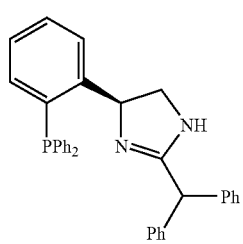
L50
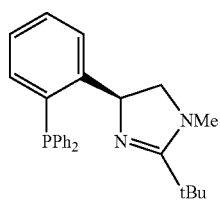
L51
Scheme 4
-continued
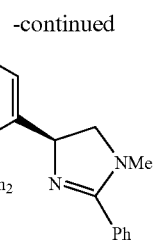
L52
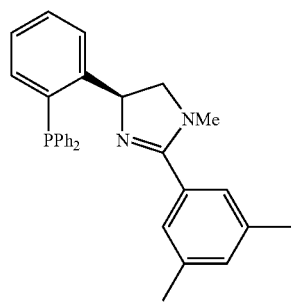
L53
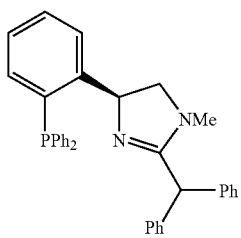
L54
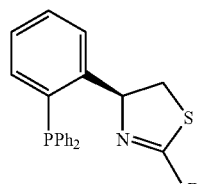
L55
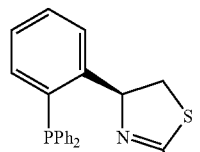
L56
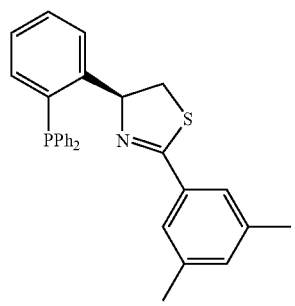
L57

-continued

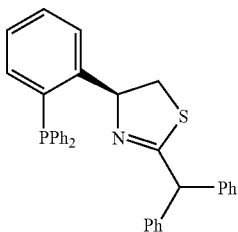
L58

The present invention also provides a catalyst formed from the above ligands and a transition metal, a salt thereof, or a complex thereof.

The catalyst is prepared by a process including:

contacting a transition metal, a salt thereof, or a complex thereof, and a chiral ligand selected from compounds represented by the following formulas and their enantiomers:

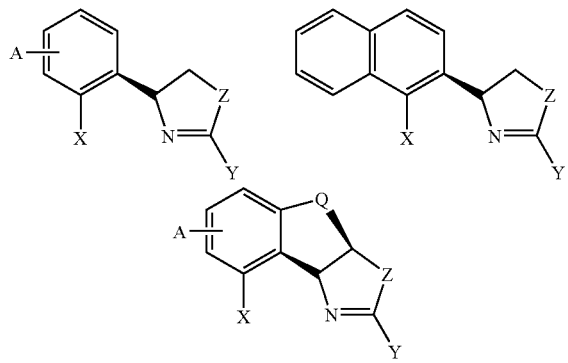

where X is selected from:

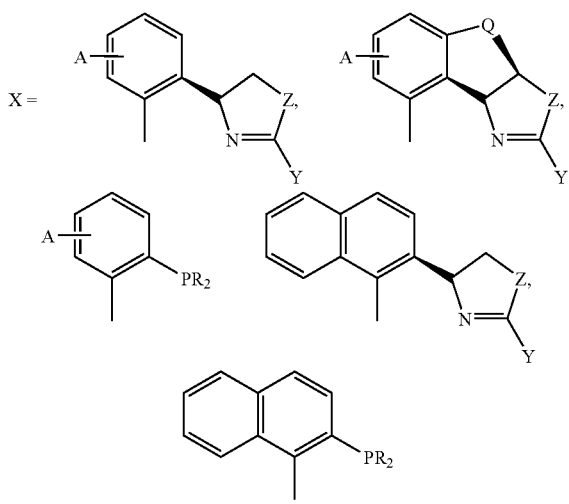

$PR_2$, $P(OR)_2$, $P(NR_2)_2$, $PCl_2$, phosphocycle, P-chiral phospholane$_2$, Cl, Br, I, OH, SR, $NH_2$, COOR, COOH, and R;

wherein each R is independently selected from: linear, branched or cyclic alkyl, linear, branched or cyclic substituted alkyl, aryl, substituted aryl, and a hetereocyclic group;

wherein Y is selected from: linear, branched or cyclic alkyl, linear, branched or cyclic substituted alkyl, aryl, substituted aryl, ferrocene, substituted ferrocene, a hetereocyclic group, and a hetereoaromatic group;

A is a substituent on the aromatic ring selected from: hydrogen, halide, alkoxyl, carboxylates, linear, branched or cyclic alkyl, aryl, and a substituted aryl group;

Z is selected from: oxygen, sulfur, NH, NR, and $CH_2$; and

Q is selected from: $CH_2$ and $CH_2CH_2$.

Preferably, the catalyst is a non-racemic mixture of enantiomers. More preferably, the catalyst is one of the enantiomers. The catalyst can be prepared in situ or as an isolated compound.

Preferably, the transition metal is selected from: Fe, Zn, Mn, Co, Cu, Ag, Ni, Pt, Pd, Rh, Ru, Ir, Re, Mo, Ti, and V and the transition metal salt, or complex thereof, can be a salt or complex of any of Fe, Zn, Mn, Co, Cu, Ag, Ni, Pt, Pd, Rh, Ru, Ir, Re, Mo, Ti, or V, and can include compounds, such as, $FeX_3$; $Fe(OTf)_3$; $Fe(OAc)_3$; $Mn(OAc)_3$; $Mn(OTf)_3$; $MnX_3$; $Zn(OTf)_2$; $Co(OAc)_2$, AgX; Ag(OTf); $Ag(OTf)_2$; AgOAc; $PtCl_2$; $H_2PtCl_4$; $Pd_2(DBA)_3$; $Pd(OAc)_2$; $PdCl_2(RCN)_2$; $(Pd(allyl)Cl)_2$; $Pd(PR_3)_4$; $(Rh(NBD)_2)X$; $(Rh(NBD)Cl)_2$; $(Rh(COD)Cl)_2$; $(Rh(COD)_2)X$; $Rh(acac)(CO)_2$; $Rh(ethylene)_2(acac)$; $(Rh(ethylene)_2Cl)_2$; $RhCl(PPh_3)_3$; $Rh(CO)_2Cl_2$; $RuHX(L)_2(PN)$, $RuX_2(L)_2(PN)$, $Ru(arene)X_2(PN)$, Ru(aryl group)$X_2$; $Ru(RCOO)_2(PN)$; $Ru(methallyl)_2(PN)$; Ru(aryl group)$X_2(PPh_3)_3$; Ru(COD)(COT); Ru(COD)(COT)X; $RuX_2(cymen)$; $Ru(COD)n$; Ru(aryl group)$X_2(PN)$; $RuCl_2(COD)$; $(Ru(COD)_2)X$; $RuX_2(PN)$; $RuCl_2(=CHR)(PR'_3)_2$; $Ru(ArH)Cl_2$; $Ru(COD)(methallyl)_2$; $(Ir(NBD)_2Cl)_2$; $(Ir(NBD)_2)X$; $(Ir(COD)_2Cl)_2$; $(Ir(COD)_2)X$; CuX $(NCCH_3)_4$; Cu(OTf); $Cu(OTf)_2$; Cu(Ar)X; CuX; $Ni(acac)_2$; $NiX_2$; (Ni (allyl)X)$_2$; $Ni(COD)_2$; $MoO_2(acac)_2$; $Ti(OiPr)_4$; $VO(acac)_2$; $MeReO_3$; $[Rh(COD)Cl]_2$; $[Rh(COD)_2]X$ (X=$BF_4$, $ClO_4$, $SbF_6$, $CF_3SO_3$, $BAr_4$ etc); $[Ir(COD)Cl]_2$; and $[Ir(COD)_2]X$ (X=$BF_4$, $ClO_4$, $SbF_6$, or $CF_3SO_3$); wherein each R and R' is independently selected from: alkyl and aryl; wherein Ar is an aryl group; wherein PN is the chiral ligand according to the present invention; wherein L is a solvent; and X is a counter anion selected from: halogen, $BF_4$, $B(Ar)_4$ wherein Ar is fluorophenyl or 3,5-di-trifluoromethyl-1-phenyl, $ClO_4$, $SbF_6$, $PF_6$, $CF_3SO_3$, RCOO and a mixture thereof.

The transition metal complexes according to the present invention are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition.

Accordingly, the present invention provides a method of preparing an asymmetric compound by a transition metal catalyzed asymmetric reaction, which can be hydrogenation, hydride transfer reaction, hydrosilylation, hydroboration, hydrovinylation, hydroformylation, hydrocarboxylation, allylic alkylation, epoxidation, cyclopropanation, Diels-Alder reaction, Aldol reaction, ene reaction, Heck reaction or Michael addition.

The method includes the step of: contacting a substrate and a reactant for an asymmetric reaction in the presence of a catalyst at a temperature, pressure and for a length of time sufficient to produce the asymmetric compound. The asymmetric reaction is selected from: hydrogenation, hydride transfer reaction, hydrosilylation, hydroboration, hydrovinylation, hydroformylation, hydrocarboxylation, allylic alkylation, epoxidation, cyclopropanation, Diels-Alder reaction, Aldol reaction, ene reaction, Heck reaction and Michael addition. The catalyst can be prepared by a process including: contacting a transition metal, a salt thereof, or a complex thereof, and a chiral ligand selected from compounds represented by the following formulas and their enantiomers:

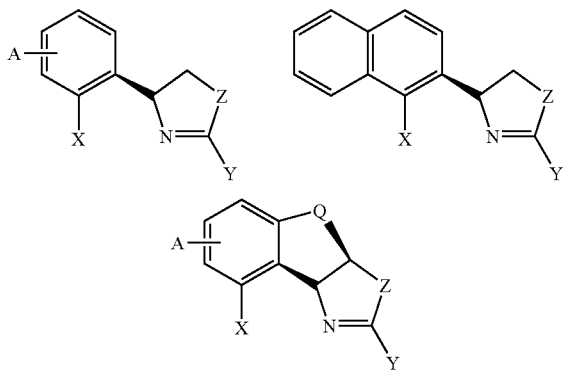

where X is selected from:

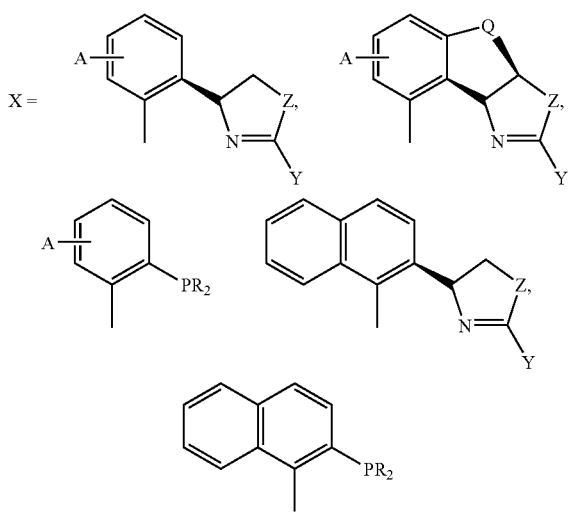

PR$_2$, P(OR)$_2$, P(NR$_2$)$_2$, PCl$_2$, phosphocycle, P-chiral phospholane$_2$, Cl, Br, I, OH, SR, NH$_2$, COOR, COOH, and R; wherein each R is independently selected from: linear, branched or cyclic alkyl, linear, branched or cyclic substituted alkyl, aryl, substituted aryl, and a hetereocyclic group; wherein Y is selected from: linear, branched or cyclic alkyl, linear, branched or cyclic substituted alkyl, aryl, substituted aryl, ferrocene, substituted ferrocene, a hetereocyclic group, and a hetereoaromatic group; wherein A is a substituent on the aromatic ring selected from: hydrogen, halide, alkoxyl, carboxylates, linear, branched or cyclic alkyl, aryl, and a substituted aryl group; wherein Z is selected from: oxygen, sulfur, NH, NR, and CH$_2$; and wherein Q is selected from: CH$_2$ and CH$_2$CH$_2$.

Preferably, the substrate is selected from: an olefin, imine, enamide and ketone; wherein the reactant is hydrogen; wherein the transition metal is Ir; and wherein the transition metal catalyzed asymmetric reaction is hydrogenation.

The present invention also provides a process for preparing these ligands, which includes an ortho-substitution reaction step. The process includes the step of:

contacting:

(i) a chiral compound selected from compounds represented by the following formulas and their enantiomers:

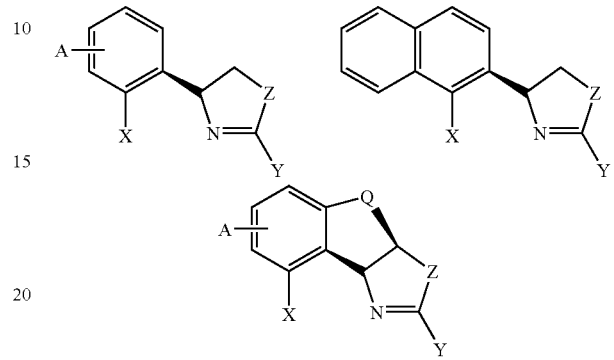

where X is a leaving group; and (ii) an a compound of the formula M-W, wherein M is a metal selected from: Li, Na, Cu, and MgX; and wherein W is anion selected from:

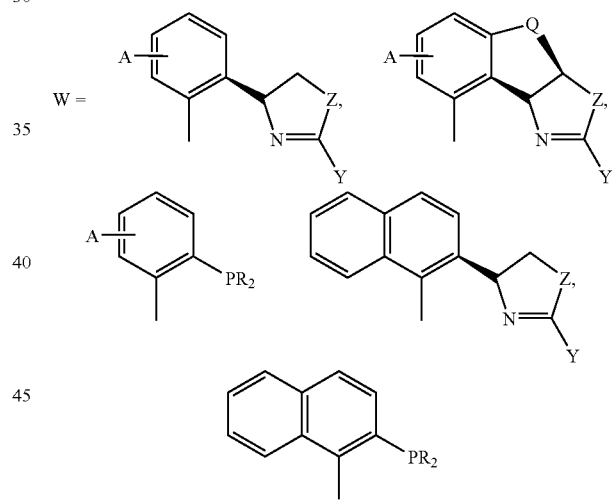

—PR$_2$, —P(OR)$_2$, —P(NR$_2$)$_2$, phosphocycle, P-chiral phospholane$_2$, —SR, NR$_2$, and R; wherein each R is independently selected from: linear, branched or cyclic alkyl, linear, branched or cyclic substituted alkyl, aryl, substituted aryl, and a hetereocyclic group; wherein Y is selected from: linear, branched or cyclic alkyl, linear, branched or cyclic substituted alkyl, aryl, substituted aryl, ferrocene, substituted ferrocene, a hetereocyclic group, and a hetereoaromatic group; wherein A is a substituent on the aromatic ring selected from: hydrogen, halide, alkoxyl, carboxylates, linear, branched or cyclic alkyl, aryl, and a substituted aryl group; wherein Z is selected from: oxygen, sulfur, NH, NR, and CH$_2$; and wherein Q is selected from: CH$_2$ and CH$_2$CH$_2$;

wherein the contacting is carried out at a temperature, pressure and for a length of time sufficient to produce the chiral ligand.

Preferably, the leaving group is selected from: halogen, trifluoromethanesulfonate, and benzenesulfonate.

The following non-limiting examples are illustrative of the various embodiments of the present invention. It is within the ability of a person of ordinary skill in the art to select other variable from among the many known in the art without departing from the scope of the present invention. Accordingly, these examples shall serve to further illustrate the present invention, not to limit them.

General Procedures

All reactions and manipulations were performed in a nitrogen-filled glove box or using standard Schlenk techniques. THF and toluene were dried and distilled from sodium benzophenoneketyl under nitrogen. Methylene chloride was distilled from $CaH_2$. Methanol was distilled from Mg under nitrogen. (R,R)—BDNPB was made a solution of 10 mg/ml in toluene before use.

Column chromatography was performed using EM silica gel 60 (230~400 mesh). $^1H$, $^{13}C$ and $^{31}P$ NMR were recorded on Bruker WP-200, AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Helwett-Packard 6890 gas chromatography using chiral capillary columns. HPLC analysis was carried on Waters™ 600 chromatography.

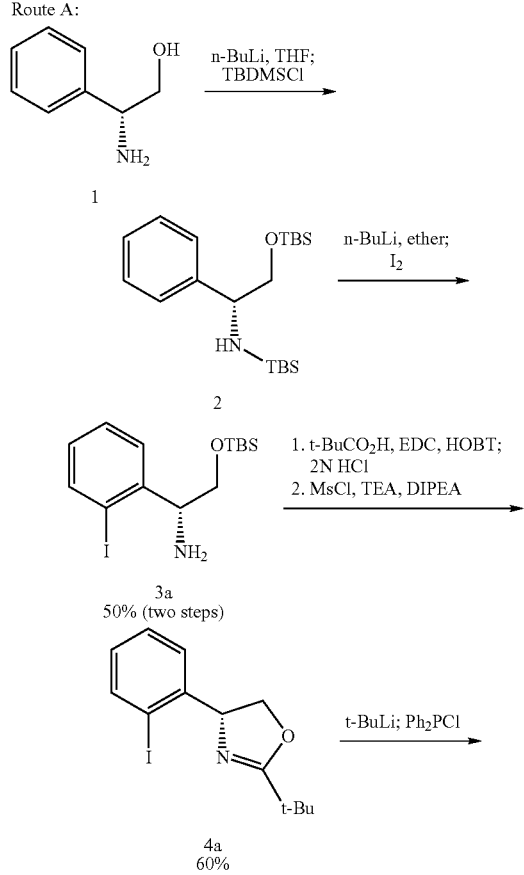

Scheme 1
Route A:

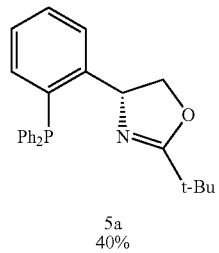

Route B:

Scheme 2

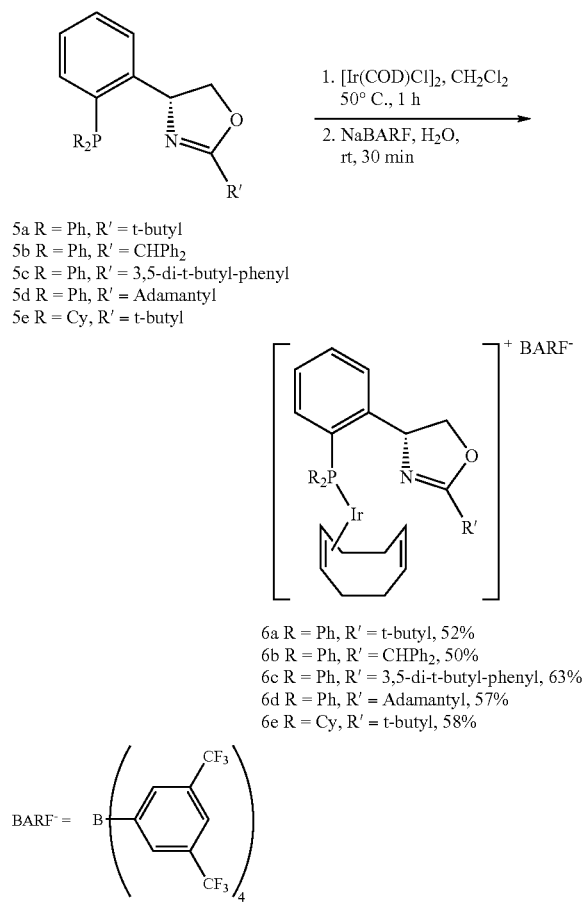

5a R = Ph, R′ = t-butyl
5b R = Ph, R′ = CHPh₂
5c R = Ph, R′ = 3,5-di-t-butyl-phenyl
5d R = Ph, R′ = Adamantyl
5e R = Cy, R′ = t-butyl 6a R = Ph, R′ = t-butyl, 52%
6b R = Ph, R′ = CHPh₂, 50%
6c R = Ph, R′ = 3,5-di-t-butyl-phenyl, 63%
6d R = Ph, R′ = Adamantyl, 57%
6e R = Cy, R′ = t-butyl, 58%

Asymmetric Hydrogenations Using Complexes 6a-6e:

TABLE 1

Asymmetric Hydrogenation of Methylstilbene Derivatives with Ir-Complex 6

| Entry | R | Catalyst | H₂ Pressure | Temp. | Conv. [%] | ee [%] (Config.) |
|---|---|---|---|---|---|---|
| 1 | H | 6a | 10 bar | rt | 31.3 | 98.4 (R) |
| 2 | H | 6a | 50 bar | rt | 64.3 | 97.8 (R) |
| 3 | H | 6a | 90 bar | rt | 94.4 | 97.0 (R) |
| 4 | H | 6a | 50 bar | 50° C. | 97.9 | 97.7 (R) |
| 5 | H | 6b | 50 bar | rt | 77.3 | 83.2 (R) |
| 6 | H | 6c | 50 bar | rt | 68.2 | 96.6 (R) |
| 7 | H | 6d | 50 bar | rt | 97.6 | 97.0 (R) |
| 8 | H | 6e | 50 bar | rt | >99.9 | 98.5 (R) |
| 9 | H | 6e | 100 bar | rt | >99.9 | 98.0 (R) |
| 10 | OMe | 6a | 100 bar | rt | >99.9 | 97.3 (R) |
| 11 | OMe | 6d | 100 bar | rt | >99.9 | 97.0 (R) |
| 12 | OMe | 6e | 100 bar | rt | >99.9 | 89.7 (R) |

TABLE 2

Asymmetric Hydrogenation of β-Methylcinnamic Esters with Ir-Complex 6

| Entry | R | Catalyst | H₂ Pressure | Temp. | Conv. [%] | ee [%] (Config.) |
|---|---|---|---|---|---|---|
| 1 | H | 6a | 100 bar | rt | 99.4 | 98.1 (R) |
| 2 | H | 6d | 100 bar | rt | 99.5 | 98.8 (R) |
| 3 | H | 6d | 50 bar | rt | 91.9 | 98.7 (R) |
| 4 | H | 6e | 100 bar | rt | >99.9 | 90.8 (R) |
| 5 | H | 6e | 50 bar | rt | 97.3 | 90.0 (R) |
| 6 | F | 6a | 100 bar | rt | 31.6 | 88.5 (R) |
| 7 | F | 6d | 100 bar | rt | 58.1 | 90.9 (R) |
| 8 | F | 6d | 100 bar | 50° C. | 89.7 | 95.6 (R) |
| 9 | F | 6e | 100 bar | rt | 94.2 | 85.4 (R) |
| 10 | OMe | 6a | 100 bar | rt | 63.7 | 80.7 (R) |
| 11 | OMe | 6d | 100 bar | rt | 96.7 | 90.2 (R) |
| 12 | OMe | 6d | 100 bar | 50° C. | 95.6 | 93.6 (R) |
| 13 | OMe | 6e | 100 bar | rt | >99.9 | 88.8 (R) |

TABLE 3

Asymmetric Hydrogenation of β-Methylcinnamic Esters with Ir-Complex 6 (R = Ad)

Ar—C(Me)=CH—COOMe (E)  →  S/C = 100, CH$_2$Cl$_2$, H$_2$, 100 bar, 50° C.  →  Ar—*CH(Me)—CH$_2$—COOMe (R)

| Ar substrate | conv. | ee |
|---|---|---|
| Ph | 99.4% | 98.8% |
| 4-F-C$_6$H$_4$ | 89.7% | 95.6% |
| 4-Cl-C$_6$H$_4$ | 86.7% | 97.6% |
| 4-Me-C$_6$H$_4$ | >99.9% | 98.3% |
| 3-Me-C$_6$H$_4$ | >99.9% | 99.4% |
| 4-MeO-C$_6$H$_4$ | 95.6% | 93.6% |
| 4-F$_3$CO-C$_6$H$_4$ | 83.9% | 95.4% |

EXPERIMENTAL SECTION 2-(tert-Butyl-dimethyl-silanyloxy)-(1R)-(2-iodo-phenyl)-ethylamine 3a. To a suspension of (S)-α-methylbenzylamine (1.37 g, 10.0 mmol) in 40 mL THF at −78° C. was added n-BuLi (2.5 M solution in hexane, 8 mL) dropwise. The resulting purple solution was stirred at −78° C. for 30 min before a solution of TBDMSCI (3.17 g, 21.0 mmol) in 20 mL THF was added at the same temperature. The reaction mixture was allowed to warm to rt naturally and was stirred overnight. After removing the THF solvent under reduced pressure, the residue was redissolved in 50 mL ether. To this solution at −78 ° C. was added n-BuLi (2.5 M solution in hexane, 8 mL) dropwise. The reaction mixture was allowed to slowly warm to rt during 3 h and stirred at rt for 1 h. I$_2$ (2.80 g, 11.0 mmol) was added at −78° C. and the reaction mixture was allowed to warm to rt and stirred at rt for 1 h. 10% Na$_2$S$_2$O$_3$ solution (20 mL) was added and the resulting mixture was stirred vigorously for 10 min. After usual work up, the product 3a was isolated by flash column chromatography (hexane:EtOAc=90:10) as a brown oil (1.89 g, 50%). [α]$^{20}_D$=−49.4 (c=0.82, CHCl$_3$); $^1$H NMR (CDCl$_3$, 360 MHz) δ 7.79 (dd, J=1.1 Hz, J=7.9 Hz, 1H), 7.57 (dd, J=1.6 Hz, J=7.8 Hz, 1H), 7.32 (dt, J=1.0 Hz, J=7.8 Hz, 1H), 6.93 (dt, J=1.7 Hz, J=7.7 Hz, 1H), 4.33 (dd, J=3.6 Hz, J=7.9 Hz, 1H), 3.80 (dd, J=3.6 Hz, J=9.9 Hz, 1H), 3.42 (dd, J=7.9 Hz, J=9.9 Hz, 1H), 1.82 (s, 2H), 0.91 (s, 9H), 0.07 (s, 3H), 0.03 (s, 3H); $^{13}$C NMR (CDCl$_3$, 90 MHz) δ 144.5, 139.5, 129.1, 128.3, 99.9, 67.6, 60.9, 26.1, 18.4, −5.1, −5.2; HRMS (M$^+$+1) m/z calculated for C$_{14}$H$_{25}$NOSiI 378.07447, found 378.07638.

2-(tert-Butyl-dimethyl-silanyloxy)-(1R)-[2-(diphenyl-phosphinothioyl)-phenyl]-ethylamine 3b. To a suspension of (S)-α-methylbenzylamine (1.37 g, 10.0 mmol, 1 equiv) in 40 mL THF at −78 ° C. was added n-BuLi (2.5 M solution in hexane, 8 mL) dropwise. The resulting purple solution was stirred at −78° C. for 30 min before a solution of TBDMSCI (3.17 g, 21.0 mmol) in 20 mL THF was added at the same temperature. The reaction mixture was allowed to warm to rt naturally and stirred overnight. After removing the THF solvent under reduced pressure, the residue was redissolved in 50 mL ether. To this solution at −78° C. was added n-BuLi (2.5 M solution in hexane, 8 mL) dropwise. The reaction mixture was allowed to slowly warm to rt during 3 h and stirred at rt for 1 h. Diphenylchlorophosphine (2.43 g, 11.0 mmol) was slowly added at −78° C. and the resulting solution was allowed to warm to rt and stirred overnight. Sulfur (0.480 g, 15.0 mmol) was added at rt and the mixture was stirred for 1 h before water was added. After usual work up, the product 3b was isolated by flash column chromatography (hexane:EtOAc=90:10) as a white solid (2.10 g, 45%). [α]$^{20}_D$=−66.6 (c=1.6, CHCl$_3$); $^1$H NMR (360 MHz, CDCl$_3$) δ 7.85-7.74 (m, 5H), 7.56-7.46 (m, 7H), 7.14 (m, 1H), 6.87 (dd, J=7.8 Hz, J=14.7 Hz, 1H), 4.80 (dd, J=3.6 Hz, J=8.0 Hz, 1H), 3.60-3.47 (m, 2H), 1.73 (s, 2H), 0.83 (s, 9H), −0.04 (s, 3H), −0.07 (s, 3H); $^{13}$C NMR (75 MHz, CDCl$_3$) δ 147.2 (d, J=9.0 Hz), 133.5-131.6 (m), 130.2 (d, J=10.2 Hz), 128.6 (d, J=1.2 Hz), 128.4 (d, J=1.6 Hz), 126.8 (d, J=12.7 Hz), 66.9, 53.6 (d, J=7.0 Hz), 25.8, 18.2, −5.3, −5.5; $^{31}$P NMR (145 MHz, CDCl$_3$) δ 42.11; HRMS (M$^+$+1) m/z calculated for C$_{26}$H$_{35}$NOSiPS 468.19408, found 468.19092.

2-(tert-Butyl-dimethyl-silanyloxy)-(1R)-[2-(dicyclo-hexyl-phosphinothioyl)-phenyl]-ethylamine 3c. To a suspention of (S)-α-methylbenzylamine (0.343 g, 2.50 mmol, 1 equiv) in 10 mL THF at −78° C. was added n-BuLi (2.5 M solution in hexane, 2 mL) dropwise. The resulting purple solution was stirred at −78° C. for 30 min before a solution of TBDMSCI (0.791 g, 5.25 mmol) in 5 mL THF was added at the same temperature. The reaction mixture was allowed to warm to rt naturally and was stirred overnight. After removing the THF solvent under reduced pressure, the residue was redissolved in 15 mL ether. To this solution at −78° C. was added n-BuLi (2.5 M solution in hexane, 2 mL) dropwise. The reaction mixture was allowed to slowly warm to rt during 3 h and was stirred at rt for 1 h. Dicyclohexylchlorophosphine (0.640 g, 2.75 mmol) was slowly added at −78° C. and the resulting solution was allowed to warm to rt and was stirred overnight. Sulfur (0.120 g, 3.75 mmol) was added at rt and the mixture was stirred for 1 h before water was added. After usual work up, the product 3c was isolated by flash column chromatography (hexane:EtOAc=90:10) as a yellow oil (0.480 g, 40%). $[\alpha]^{20}{}_D$=−48.6 (c=1.1, CHCl$_3$); $^1$H NMR (CDCl$_3$, 360 MHz) δ 8.00 (br s, 1H), 7.72-7.69 (m, 1H), 7.52-7.47 (m, 1H), 7.38-7.34 (m, 1H), 5.18 (brs, 1H), 3.82-3.70 (m, 2H), 2.41-2.35 (m, 2H), 2.11-2.08 (m, 2H), 1.87-1.19 (m, 20H), 0.95 (s, 9H), 0.11 (s, 6H); $^{13}$C NMR (CDCl$_3$, 90 MHz) δ147.1, 133.5 (m), 130.9, 128.5 (m), 127.0, 126.6, 126.5, 126.3, 68.2, 53.1, 39.8 (d, J=44.6 Hz), 39.3 (d, J=48.9 Hz), 27.0, 26.8, 26.4-26.1 (m), 25.7, 25.5, 18.0, −5.4, −5.5; $^{31}$P NMR (CDCl$_3$, 145 MHz) δ 61.43 (br s); HRMS (M$^+$+1) m/z calculated for C$_{26}$H$_{46}$NOSiPS 480.28798, found 480.28543.

General procedure for preparation of 2-adamantan-1-yl-(4R)-[2-(diphenyl-phosphinothioyl)-phenyl]-4,5-dihydro-oxazole 4d (analogously 4a-4e). A mixture of 3b (437 mg, 0.934 mmol), EDC.HCl (357 mg, 1.87 mmol), HOBT.H$_2$O (126 mg, 0.934 mmol), 1-adamantanecarboxylic acid (168 mg, 0.934 mmol), and triethylamine (0.53 mL, 3.7 mmol) in 10 mL DMF was stirred at 70° C. overnight. To the cooled mixture was added 10 mL 2N HCl solution followed by
20 mL EtOAc. The resulting mixture was stirred at rt for 30 min and then the two layers were separated. The aqueous layer was extracted with EtOAc (10 mL×2). The combined organic layer was washed with water and brine, dried with Na$_2$SO$_4$. After removal of the solvent, the resulting residue was purified by column flash chromatography (hexane:EtOAc:CH$_2$Cl$_2$=70:20:10) to give condensation product as a white solid (336 mg). To a mixture of the above condensation product (316 mg, 0.613 mmol), diisopropylethylamine (0.73 mL, 2.5 mmol) and triethylamine (0.51 mL, 6.1 mmol) in 10 mL CH$_2$Cl$_2$, was added methanesulfonylchloride (95 µL, 1.2 mmol) at 0° C. The resulting mixture was allowed to warm to rt and stirred overnight. After removal of solvent and excessive diisopropylethylamine and triethylamine under reduced pressure, 4d was isolated by column flash chromatography (hexane:EtOAc=85:15) as a white solid (235 mg, 54% two steps). $[\alpha]^{20}{}_D$=+9.35 (c=0.77, CHCl$_3$); $^1$H NMR (CDCl$_3$, 360 MHz) δ 7.83-7.66 (m, 4H), 7.52-7.40 (m, 7H), 7.32 (dd, J=4.8 Hz, J=6.8 Hz, 1H), 7.12 (m, 1H), 6.85 (ddd, J=0.7 Hz, J=7.8 Hz, J=14.8 Hz, 1H), 5.74 (t, J=9.0 Hz, 1H), 4.49 (dd, J=9.0 Hz, J=9.9 Hz, 1H), 3.78 (t, J=8.4 Hz, 1H), 1.98 (s, 3H), 1.91 (s, 6H), 1.69 (s, 6H); $^{13}$C NMR (CDCl$_3$, 75 MHz) δ 175.5, 147.4 (d, J=8.5 Hz), 133.0 (d, J=5.5 Hz), 132.7-132.3 (m), 131.9-131.7 (m), 131.6 (d, J=2.9 Hz), 130.5 (d, J=83.4 Hz), 128.8-128.4 (m), 126.7 (d, J=12.5 Hz), 75.3, 66.6 (d, J=7.0 Hz), 39.6, 36.5, 35.3, 27.8; $^{31}$P NMR (CDCl$_3$, 145 MHz) δ 42.30; HRMS (M$^+$+1) m/z calculated for C$_{31}$H$_{33}$NOPS 498.20150, found 498.19902.

2-tert-Butyl-(4R)-(2-iodo-phenyl )-4,5-dihydro-oxazole 4a. This compound was produced by the same method used for 4d as a colorless oil (60%). $[\alpha]^{20}{}_D$=−87.5 (c=1.3, CHCl$_3$); $^1$H NMR (CDCl$_3$, 360 MHz) δ 7.79 (dd, J=1.2 Hz, J=7.9 Hz, 1H), 7.32 (dt, J=1.2 Hz, J=7.7 Hz, 1H), 7.20 (dd, J=1.7 Hz, J=7.8 Hz, 1H), 6.94 (dt, J=1.8 Hz, J=7.6 Hz, 1H), 5.37 (dd, J=7.8, J=10.3 Hz, 1H), 4.76 (dd, J=8.5 Hz, J=10.3 Hz, 1H), 3.85 (t, J=8.1Hz, 1H), 1.32 (s, 9H); $^{13}$C NMR (CDCl$_3$, 90 MHz) δ 176.3, 146.0, 139.2, 129.1 (d, J=22.0 Hz), 128.6, 127.4, 98.3, 74.3, 72.8, 33.6, 28.1; HRMS (M$^+$+1) m/z calculated for C$_{13}$H$_{17}$NOI 330.03494, found 330.03633.

2-Benzhydryl-(4R)-[2-(diphenyl-phosphinothioyl)-phenyl]-4,5-dihydro-oxazole 4b. This compound was produced by the same method used for 4d as a white solid (52%). $[\alpha]^{20}{}_D$=+35.4 (c=0.65, CHCl$_3$); $^1$H NMR (CDCl$_3$, 360 MHz) δ 7.83-7.71 (m, 4H), 7.56-7.45 (m, 7H), 7.41-7.24 (m, 11H), 7.16 (m, 1H), 6.87 (dd, J=7.7 Hz, J=14.8 Hz, 1H), 5.91 (t, J=9.1 Hz, 1H), 5.26 (s, 1H), 4.72 (t, J=9.6 Hz, 1H), 3.96 (t, J=8.5 Hz, 1H); $^{13}$C NMR (CDCl$_3$, 75 MHz) δ 169.4, 146.8 (d, J=8.5 Hz), 139.2 (d, J=8.7 Hz), 133.1-130.1 (m), 129.0-128.5 (m), 127.2 (d, J=4.2 Hz), 127.0 (d, J=12.5 Hz), 76.3, 66.8 (d, J=7.2 Hz), 51.2; $^{31}$P NMR (CDCl$_3$, 145 MHz) δ 42.38; HRMS (M$^+$+1) m/z calculated for C$_{34}$H$_{29}$NOPS 530.17020, found 530.17347.

2-(3,5-Di-tert-butyl-phenyl)-(4R)-[2-(diphenyl-phosphinothioyl)-phenyl]-4,5-dihydro-oxazole 4c. This compound was produced by the same method used for 4d as a white solid (50%). $[\alpha]^{20}{}_D$=+34.0 (c=1.1, CHCl$_3$); $^1$H NMR (CDCl$_3$, 360 MHz) δ 7.92-7.76 (m, 6H), 7.57-7.49 (m, 9H), 7.19 (t, J=7.4 Hz, 1H), 6.95 (dd, J=7.7 Hz, J=14.8 Hz, 1H), 6.03 (t, J=8.9 Hz, 1H), 4.72 (t, J=9.7 Hz, 1H), 4.07 (t, J=8.5 Hz, 1H), 1.35 (s, 18H); $^{13}$C NMR (CDCl$_3$, 90 MHz) δ 166.6, 151.1, 147.5 (d, J=8.5 Hz), 133.4-131.6 (m), 130.7, 129.6-129.0 (m), 127.1, 125.9, 123.0, 75.9, 68.0, 35.2, 31.6; $^{31}$P NMR (CDCl$_3$, 145 MHz) δ 42.30; HRMS (M$^+$+1) m/z calculated for C$_{35}$H$_{39}$NOPS 552.24845, found 552.24701.

2-tert-Butyl-(4R)-[2-(dicyclohexyl-phosphinothioyl)-phenyl]-4,5-dihydro-oxazole 4e. This compound was produced by the same method used for 4d as a colorless oil (52%). $[\alpha]^{20}{}_D$=−78.0 (c=0.50, CHCl$_3$); $^1$H NMR (CDCl$_3$, 300 MHz) δ 7.54-7.49 (m, 2H), 7.37-7.31 (m, 2H), 6.53 (m, 1H), 4.94 (t, J=9.5 Hz, 1H), 3.92 (t, J=8.0 Hz, 1H), 2.54 (m, 1H), 2.31 (m, 1H), 2.09 (m, 1H), 1.91-1.13 (m, 19H), 1.34 (s, 9H); $^{13}$C NMR (CDCl$_3$, 75 MHz) δ 175.7, 149.2, 131.7 (d, J=2.6 Hz), 131.3, 128.6 (d, J=9.0 Hz), 126.3 (d, J=10.5 Hz), 125.0 (d, J=63.8 Hz), 76.2, 66.5 (d, J=3.7 Hz), 41.2 (d, J=48.2 Hz), 36.5 (d, J=51.2 Hz), 33.3, 27.9, 26.6-25.2 (m); $^{31}$P NMR (CDCl$_3$, 145 MHz) δ 57.27 (br); HRMS (M$^+$+1) m/z calculated for C$_{25}$H$_{39}$NOPS 432.24845, found 432.24619.

2-tert-Butyl-(4R)-(2-diphenylphosphanyl-phenyl)-4,5-dihydro-oxazole 5a. To a solution of 4a (94 mg, 0.286 mmol) in 4 mL ether was added t-BuLi (1.7 M solution, 0.34 mL) at −78° C. The reaction mixture was stirred at −78° C. for 30 min before diphenylchlorophosphine (2.43 g, 11.0 mmol) was added slowly. The solution was allowed to warm to rt and was stirred overnight. Water was added. The aqueous layer was separated and extracted with CH$_2$Cl$_2$. The combined organic layers were dried with Na$_2$SO$_4$ and concentrated. The residue was purified by flash column chromatography to give 5a as a colorless oil (40%). $[\alpha]^{20}{}_D$=−50.9 (c=2.0, CHCl$_3$); $^1$H NMR (CD$_2$Cl$_2$, 360 MHz) δ 7.40-7.26 (m, 12H), 7.19 (dt, J=1.5 Hz, J=7.5 Hz, 1H), 6.93-6.89 (m, 1H), 5.82-5.75 (m, 1H), 4.24 (dd, J=is 8.4 Hz, J=10.2 Hz, 1H), 3.64 (dt, J=0.5 Hz, J=8.4 Hz, 1H), 1.28 (s, 9H); $^{13}$C NMR (CD$_2$Cl$_2$, 90 MHz) δ 175.8, 148.4 (d, J=24.0 Hz), 136.9 (d, J=10.2 Hz), 135.4-134.2 (m), 130.0-129.3 (m), 127.9 (br s), 126.8 (br s), 75.4 (d, J=4.4 Hz), 67.5 (m), 33.9, 28.3; $^{31}$P NMR (CD$_2$Cl$_2$, 145 MHz) δ-14.97; HRMS (M$^+$+1) m/z calculated for C$_{25}$H$_{27}$NOP 388.18248, found 388.17930.

General procedure for preparation of 2-adamantan-1-yl-(4R)-(2-diphenylphosphanyl-phenyl)-4,5-dihydro-oxazole 5d (analogously 5b-5e). To a N$_2$-flushed Schlenk flask was loaded about 1 g of Raney Ni 2800 slurry. The Raney Ni was washed sequentially with methanol (3 mL×3), ether (3 mL×3), and dried degassed CH$_3$CN (3 mL×3). To this flask was then transferred a solution of 4d (190 mg, 0.382 mmol) in 6 mL CH$_3$CN. The resulting mixture was stirred under N$_2$ at rt for 1 d. The mixture was filtered under N$_2$. The Raney Ni solid was washed with CH$_3$CN (3 mL×3). The combined filtrate was concentrated under reduced pressure and the residue was passed through a short silica gel plug under N$_2$ to give pure product 5d as a white solid (91%). $[\alpha]^{20}{}_D$=−66.1 (c=0.75, CHCl$_3$); $^1$H NMR (CDCl$_3$, 300 MHz) δ 7.31-7.05

(m, 12H), 6.79 (ddd, J=0.9 Hz, J=4.4 Hz, J=7.8 Hz, 1H), 5.74 (ddd, J=5.1 Hz, J=8.3 Hz, J=13.4 Hz, 1H), 4.15 (dd, J=8.5 Hz, J=10.3 Hz, 1H), 3.53 (t, J=8.3 Hz, 1H), 1.96 (s, 3H), 1.90 (s, 6H), 1.66 (s, 6H); $^{13}$C NMR (CDCl$_3$, 75 MHz) δ 175.2, 147.8 (d, J=24.3 Hz), 136.4-136.1 (m), 134.7, 134.4, 134.0, 133.7, 133.5, 129.7, 129.2, 128.9, 128.8, 128.7, 127.6, 126.1 (d, J=5.7 Hz), 74.6 (d, J=5.0 Hz), 66.8 (d, J=24.2 Hz), 39.9, 36.8, 35.6, 28.2; $^{31}$P NMR (CDCl$_3$, 145 MHz) δ-15.14; HRMS (M$^+$+1) m/z calculated for C$_{31}$H$_{33}$NOP 466.22943, found 466.22620.

2-Benzhydryl-(4R)-(2-diphenylphosphanyl-phenyl)-4,5-dihydro-oxazole 5b. This compound was produced by the same method used for 5d as a white solid (94%). [α]$^{20}_D$=−67.9 (c=0.66, CHCl$_3$); $^1$H NMR (CD$_2$Cl$_2$, 360 MHz) δ 7.44-7.21 (m, 23H), 6.98-6.95 (m, 1H), 5.97 (dt, J=5.6 Hz, J=9.4 Hz, 1H), 5.24 (s, 1H), 4.38 (dd, J=8.6 Hz, J=10.3 Hz), 3.74 (t, J=8.6 Hz); $^{13}$C NMR (CD$_2$Cl$_2$, 90 MHz) δ 169.3, 147.9 (d, J=24.4 Hz), 140.4 (d, J=3.6 Hz), 136.7 (d, J=10.3 Hz), 135.5-134.0 (m), 130.1-126.9 (m), 75.6 (d, J=5.3 Hz), 68.0, 51.7; $^{31}$P NMR (CD$_2$Cl$_2$, 145 MHz) δ-15.10; HRMS (M$^+$+1) m/z calculated for C$_{34}$H$_{29}$NOP 498.19813, found 498.19772.

2-(3,5-Di-tert-butyl-phenyl)-(4R)-(2-diphenylphosphanyl-phenyl)-4,5-dihydro-oxazole 5c. This compound was produced by the same method used for 5d as a white solid (95%). [α]$^{20}_D$=−48.3 (c=0.87, CHCl$_3$); $^1$H NMR (CD$_2$Cl$_2$, 360 MHz) δ 7.95 (d, J=1.8 Hz, 2H), 7.67 (t, J=1.8 Hz, 1H), 7.50-7), 7.43-7.34 (m, 1H), 7.24 (dt, J=1.3 Hz, J=7.5 Hz, 1H), 7.01 (ddd, J=1.1 Hz, J=4.4 Hz, J=7.6 Hz, 1H), 6.11 (ddd, J=5.9 Hz, J=8.7 Hz, J=14.5 Hz, 1H), 4.48 (dd, J=8.4 Hz, J=10.2 Hz, 1H), 3.90 (t, J=8.5 Hz, 1H), 1.42 (s, 18H); $^{13}$C NMR (CD$_2$Cl$_2$, 90 MHz) δ 166.1, 151.7, 148.2 (d, J=23.9 Hz), 137.0 (m), 135.6-133.9 (m), 130.2-126.3 (m), 123.3, 75.4 (d, J=4.2 Hz), 68.6, 35.5, 31.9; $^{31}$P NMR (CD$_2$Cl$_2$, 145 MHz) δ-14.83. HRMS (M$^+$+1) m/z calculated for C$_{35}$H$_{39}$NOP 520.27638, found 520.27501.

2-tert-Butyl-(4R)-(2-dicyclohexylphosphanyl-phenyl)-4,5-dihydro-oxazole 5e. This compound was produced by the same method used for 5d as a colorless oil (90%). [α]$^{20}_D$=−70.9 (c=0.53, CHCl$_3$); $^1$H NMR (CD$_2$Cl$_2$, 360 MHz) δ 7.49-7.47 (m, 1H), 7.37-7.24 (m, 3H), 6.02 (ddd, J=5.7 Hz, J=8.4 Hz, J=14.1 Hz, 1H), 4.76 (dd, J=8.3 Hz, J=10.3 Hz, 1H), 3.79 (t, J=8.3 Hz, 1H), 2.00-0.85 (m, 31H); $^{13}$C NMR (CD$_2$Cl$_2$, 75 MHz) δ 175.2, 151.0 (d, J=25.3 Hz), 133.2 (d, J=20.8 Hz), 133.1 (d, J=3.4 Hz), 129.5, 126.7, 126.2 (d, J=6.3 Hz), 75.9 (d, J=7.2 Hz), 67.9 (d, J=25.9 Hz), 35.2 (d, J=12.9 Hz), 34.0 (d, J=11.7 Hz), 33.7, 31.3-30.9 (m), 30.0 (d, J=10.2 Hz), 29.2 (d, J=6.2 Hz), 28.1, 27.7-27.3 (m), 26.8 (d, J=3.9 Hz); $^{31}$P NMR (CD$_2$Cl$_2$, 145 MHz) δ-14.46; HRMS (M$^+$+1) m/z calculated for C$_{25}$H$_{39}$NOP 400.27638, found 400.27262.

General procedure for preparation of complex 6d (analogously 6a-6e). To a Schlenk tube was added 5d (76 mg, 0.163 mmol), [Ir(COD)Cl]$_2$ (54.8 mg, 0.0816 mmol) and dried CH$_2$Cl$_2$ (3 mL). The resulting red solution was heated under N$_2$ at 50° C. for 1 h. TLC indicated that 5d was consumed completely. After the solution was cooled to rt, Na[BARF] (217 mg, 0.245 mmol) was added followed by H$_2$O (3 mL). The resulting mixture was stirred vigorously for 30 min. The two layers were separated and the aqueous layer was extracted with CH$_2$Cl$_2$ (3 mL×2). The combined organic layer was dried with Na$_2$SO$_4$ and evaporated. The residue was purified by flash column chromatography (hexanes: CH$_2$Cl$_2$=1:1) to give 6d as an orange solid (57%). $^1$H NMR (CD$_2$Cl$_2$, 360 MHz) δ 7.75 (s, 8H), 7.66-7.58 (m, 8H), 7.43-7.38 (m, 5H), 7.35-7.26 (m, 4H), 7.05 (m, 1H), 5.84 (dd, J=3.5 Hz, J=9.8 Hz, 1H), 5.05 (m, 1H), 5.01 (dd, J=4.0 Hz, J=9.4 Hz, 1H), 4.84 (t, J=9.6 Hz, 1H), 4.35 (m, 1H), 4.28 (m, 1H), 3.23 (m, 1H), 2.52-2.36 (m, 3H), 2.25 (m, 1H), 2.16-2.01 (m, 2H), 1.84-1.74 (m, 7H), 1.64-1.52 (m, 4H), 1.41-1.36 (m, 6H); $^{31}$P NMR (CD$_2$Cl$_2$, 145 MHz) δ 15.89; HRMS (cation) m/z calculated for C$_{39}$H$_{44}$NOPIr 766.27845, found 766.27163; HRMS (anion) m/z calculated for C$_{32}$H$_{12}$BF$_{24}$ 863.06434, found 863.07188.

6a. This compound was produced by the same method used for 6d as a yellow solid (52%). $^1$H NMR (CDCl$_3$, 360 MHz) δ 7.74 (s, 8H), 7.60-6.54 (m, 8H), 7.46-7.31 (m, 6H), 7.25-7.17 (m, 3H), 7.05 (ddd, J=1.2 Hz, J=7.9 Hz, J=10.9 Hz, 1H), 5.81 (dd, J=3.7 Hz, J=9.7 Hz, 1H), 4.96 (m, 1H), 4.94 (dd, J=4.2 Hz, J=9.4 Hz, 1H), 4.81 (t, J=9.7 Hz, 1H), 4.26 (m, 1H), 4.16 (m, 1H), 3.22 (m, 1H), 2.50-2.33 (m, 2H), 2.24 (m, 1H), 2.13-2.00 (m, 2H), 1.71 (m, 1H), 1.55 (m, 1H), 0.93 (s, 9H); $^{31}$P NMR (CDCl$_3$, 145 MHz) δ 15.55; HRMS (cation) m/z calculated for C$_{33}$H$_{38}$NOPIr 688.23150, found 688.22827; HRMS (anion) m/z calculated for C$_{32}$H$_{12}$BF$_{24}$ 863.06434, found 863.06754.

6b. This compound was produced by the same method used for 6d as a red solid (50%). $^1$H NMR (CD$_2$Cl$_2$, 360 MHz) δ 7.77-6.78 (m, 34H), 5.93 (d, J=7.2 Hz, 2H), 5.76 (dd, J=5.6 Hz, J=9.7 Hz, 1H), 5.20-5.11 (m, 2H), 4.90-4.80 (m, 2H), 3.95 (m, 1H), 3.80 (m, 1H), 3.00 (m, 1H), 2.53-2.45 (m, 2H), 2.35-2.19 (m, 2H), 1.90 (m, 1H), 1.75 (m, 1H), 1.52-1.34 (m, 2H); $^{31}$P NMR (CD$_2$Cl$_2$, 145 MHz) δ 16.33; HRMS (cation) m/z calculated for C$_{42}$H$_{40}$NOPIr 798.24715, found 798.24948; HRMS (anion) m/z calculated for C$_{32}$H$_{12}$BF$_{24}$ 863.06434, found 863.07128.

6c. This compound was produced by the same method used for 6d as an orange solid (63%). $^1$H NMR (CD$_2$Cl$_2$, 360 MHz) δ 7.79 (m, 2H), 7.73 (s, 9H), 7.62 (m, 1H), 7.56 (br s, 4H), 7.50-7.36 (m, 12H), 7.22 (m, 1H), 6.04 (dd, J=4.2 Hz, J=9.1 Hz, 1H), 5.21 (dd, J=4.4 Hz, J=9.5 Hz, 1H), 5.07 (t, J=9.4 Hz, 1H), 5.04 (m, 1H), 4.08 (m, 1H), 3.87 (m, 1H), 3.52 (m, 1H), 2.54-2.39 (m, 2H), 2.30 (m, 1H), 2.22-2.14 (m, 2H), 1.90 (m, 1H), 1.70-1.64 (m, 2H), 1.31 (s, 18H); $^{31}$P NMR (CD$_2$Cl$_2$, 145 MHz) δ 12.47; HRMS (cation) m/z calculated for C$_{43}$H$_{50}$NOPIr 820.32540, found 820.32552; HRMS (anion) m/z calculated for C$_{32}$H$_{12}$BF$_{24}$ 863.06434, found 863.06159.

6e. This compound was produced by the same method used for 6d as an orange solid (58%). $^1$H NMR (CD$_2$Cl$_2$, 360 MHz) δ 7.74 (m, 8H), 7.65-7.51 (m, 7H), 7.39 (m, 1H), 5.67 (d, J=7.2 Hz, 1H), 5.28 (dd, J=1.2 Hz, J=10.2 Hz, 1H), 5.06 (m, 1H), 4.92 (m, 1H), 4.43 (dd, J=7.5 Hz, J=10.2 Hz, 1H), 3.76 (m, 1H), 3.56 (m, 1H), 2.97 (m, 1H), 2.60-2.51 (m, 2H), 2.39-2.10 (m, 5H), 1.94-1.63 (m, 12H), 1.52-1.32 (m, 19H); $^{31}$P NMR (CD$_2$Cl$_2$, 145 MHz) δ 9.00; HRMS (cation) m/z calculated for C$_{33}$H$_{50}$NOPIr 700.32540, found 700.32349; HRMS (anion) m/z calculated for C$_{32}$H$_{12}$BF$_{24}$ 863.06434, found 863.07146.

General Hydrogenation Procedure:

α-Methyl stilbene (25.9 mg, 0.133 mmol) and Ir-complex 6d (1 mg, 0.614 µmol) was dissolved in CH$_2$CH$_2$ (2 mL). This solution was then transferred into an autoclave. The hydrogenation was performed at room temperature (or described temperature in Table 1) under 50 bar of G2 for 12 h.

After carefully releasing the hydrogen, the reaction mixture was directly passed through a short silica gel plug and flashed with ether. After evaporation, the residue was directly used for chiral HPLC analysis to measure the enantiomeric excess and for GC to measure the conversion.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

The invention claimed is:

1. A chiral ligand selected from the group consisting of compounds represented by the following formulas and their enantiomers:

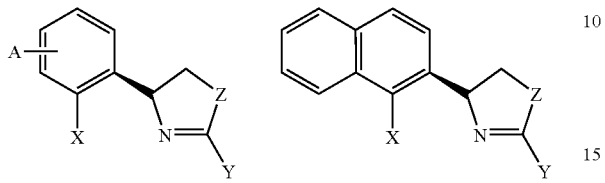

where x is $PR_2$;
wherein each R is independently selected from the group consisting of: linear, branched or cyclic alkyl, linear, branched or cyclic substituted alkyl, aryl, and substituted aryl, and a heterocyclic group;
wherein Y is selected from the group consisting of: linear, branched or cyclic alkyl, linear, branched or cyclic substituted alkyl, aryl, and substituted aryl, ferrocene, substituted ferrocene, a heterocyclic group, and a heteroaromatic group;
A is a substituent on the aromatic ring selected from the group consisting of: hydrogen, halide, alkoxyl, carboxylates, linear, branched or cyclic alkyl, aryl, and a substituted aryl group; and
Z is selected from the group consisting of: oxygen sulfur, NH, NR, and $CH_2$.

2. The chiral ligand according to claim 1, wherein:
each R is independently selected from the group consisting of: an alkyl, aryl, substituted alkyl, substituted aryl, and heterocyclic group;
Y is selected from the group consisting of: linear, branched or cyclic alkyl, linear, branched or cyclic substituted alkyl, aryl, and substituted aryl.

3. The chiral ligand according to claim 2, wherein each R and Y is independently selected from the group consisting of an alkyl of 1-12 carbon atoms.

4. The chiral ligand according to claim 3, wherein each R and Y is independently selected from the group consisting of: methyl, ethyl, propyl, butyl, pentyl, cyclopentyl, hexyl, cyclohexyl, octyl, isomers thereof.

5. The chiral ligand according to claim 2, wherein each R and Y is independently selected from the group consisting of an aryl group of 6-15 carbon atoms.

6. The chiral ligand according to claim 5, wherein each R and Y is independently selected from the group consisting of: phenyl, tolyl, mesityl, xylyl, biphenylyl and naphthyl.

7. The chiral ligand according to claim 1, wherein said ligand is selected from the group consisting of compounds represented by the following formula and its enantiomers:

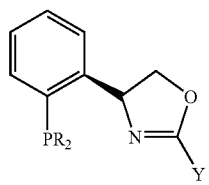

wherein each R is independently selected from the group consisting of: an alkyl, aryl, substituted alkyl, substituted aryl, and heterocyclic group; and
Y is independently selected from the group consisting of: linear, branched or cyclic alkyl, linear, branched or cyclic substituted alkyl, aryl, and substituted aryl.

8. The chiral ligand according to claim 7, wherein each R and Y is independently selected from the group consisting of an alkyl of 1-12 carbon atoms.

9. The chiral ligand according to claim 8, wherein each R and Y is independently selected from the group consisting of: methyl, ethyl, propyl, butyl, pentyl, cyclopentyl, hexyl, cyclohexyl, octyl, and isomers thereof.

10. The chiral ligand according to claim 7, wherein each R and Y is independently selected from the group consisting of an aryl group of 6-15 carbon atoms.

11. The chiral ligand according to claim 10, wherein each R and Y is independently selected from the group consisting of: phenyl, tolyl, mesityl, xylyl, biphenylyl and naphthyl.

12. The chiral ligand according to claim 1, wherein A=hydrogen, R=methyl, Y=methyl, and Z=oxygen.

* * * * *